(12) United States Patent
Molander et al.

(10) Patent No.: US 6,562,166 B2
(45) Date of Patent: May 13, 2003

(54) METHOD OF MATERIAL PROPERTY MODIFICATION WITH ULTRASONIC ENERGY

(75) Inventors: John C. Molander, Cincinnati, OH (US); D. Randell Greer, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 40 days.

(21) Appl. No.: 09/854,009

(22) Filed: May 11, 2001

(65) Prior Publication Data

US 2002/0166617 A1 Nov. 14, 2002

(51) Int. Cl.⁷ ............................................. B29C 65/08
(52) U.S. Cl. .................. 156/73.1; 156/229; 156/494; 156/580.1; 156/580.2
(58) Field of Search ............................. 156/73.1, 229, 156/290, 292, 308.2, 494, 496, 580.1, 580.2; 264/442, 443, 444

(56) References Cited

U.S. PATENT DOCUMENTS

| | | | |
|---|---|---|---|
| 3,908,808 A | 9/1975 | Busker | |
| 4,153,664 A | 5/1979 | Sabee | |
| 4,404,052 A | 9/1983 | Persson et al. | |
| 4,406,720 A | 9/1983 | Wang et al. | |
| 4,430,148 A | 2/1984 | Schaefer | |
| 4,534,818 A | * 8/1985 | Kreager et al. | 156/466 |
| 4,582,555 A | * 4/1986 | Bower | 156/290 |
| 4,650,530 A | 3/1987 | Mahoney et al. | |
| 4,668,316 A | 5/1987 | Sager | |
| 4,732,631 A | 3/1988 | Shimizu | |
| 4,863,542 A | 9/1989 | Oshefsky et al. | |
| 5,069,532 A | 12/1991 | Taylor, Jr. | |
| 5,073,216 A | 12/1991 | Siegel et al. | |
| 5,110,403 A | 5/1992 | Ehlert | |
| 5,185,052 A | 2/1993 | Chappell et al. | |
| 5,269,981 A | 12/1993 | Jameson et al. | |
| 5,314,737 A | 5/1994 | Cohen et al. | |
| 5,356,682 A | 10/1994 | Stewart et al. | |
| 5,447,588 A | 9/1995 | Merz et al. | |
| 5,466,401 A | 11/1995 | Cohen et al. | |
| 5,525,172 A | * 6/1996 | Cadiou | 156/73.1 |
| 5,707,470 A | 1/1998 | Rajala et al. | |
| 5,711,847 A | 1/1998 | Rajala et al. | |
| 5,723,087 A | 3/1998 | Chappell et al. | |
| 5,807,320 A | 9/1998 | Kammerer | |
| 5,871,605 A | 2/1999 | Bett | |
| 5,930,139 A | 7/1999 | Chapdelaine et al. | |
| 5,968,029 A | 10/1999 | Chappell et al. | |
| 5,976,315 A | * 11/1999 | Martin | 156/580.2 |
| 5,993,432 A | 11/1999 | Lodge et al. | |
| 6,089,438 A | * 7/2000 | Suzuki et al. | 228/1.1 |
| 6,379,483 B1 | * 4/2002 | Eriksson | 156/73.1 |

OTHER PUBLICATIONS

*Ultrasonics—Fundamentals, Technology, Applications*, Dale Ensminger, Marcel Dekker, Inc., ISBN 0–8247–7659–3, 2$^{nd}$ edition of reference book on ultrasonic fundamentals and applications.

* cited by examiner

Primary Examiner—James Sells
(74) Attorney, Agent, or Firm—Jeffrey R. Moore; Jay A. Krebs; Ken K. Patel

(57) ABSTRACT

A method of achieving a workpiece material property change using a horn with a set of activation teeth as a source of ultrasonic energy and an anvil with a second set of activation teeth. The workpiece is engaged in tension between the two sets of activation teeth.

27 Claims, 7 Drawing Sheets

METHOD OF MATERIAL PROPERTY MODIFICATION WITH ULTRASONIC ENERGY

FIELD OF INVENTION

The present invention is a method and ultrasonic device for modifying the physical properties of various workpiece materials through the use of ultrasonic energy.

BACKGROUND OF THE INVENTION

Garments such as disposable diapers include elastic waist or leg bands. The bands are often constructed of an elastomeric material bonded to a backing material. The backing material is commonly referred to as a web or nonwoven fibrous material. The bonds are typically ultrasonic bonds or adhesive. One problem with a bonded elastomeric and web approach is that the web material is relatively inelastic compared to the elastomeric. As a result the elasticity of the material combination is limited.

The term "Ultrasonic" generally refers to vibrations beyond the human audible sound frequencies. As employed herein, ultrasonic energy is defined as vibration energy above 16 kHz. Ultrasonic devices have been used for nondestructive testing, welding, cutting, and metal component cleaning. A sandwich type transducer driven by an electronic power supply, which is then amplified through a horn, is a common source of ultrasonic energy.

Ultrasonic energy is used to bond numerous materials. One example for bonding an elastomeric material to a web backing material is U.S. Pat. No. 4,863,542, Oshefsky et al. Oshefsky attempts to solve the problem of decreased laminate elasticity by stretching the elastomeric prior to bonding it with an inelastic web. The Oshefsky method has limitations that remain unresolved. One limitation is the bunching up of the web material when the elastic retracts. Bunching occurs when a non-elastic web material is partially bonded to a stretched elastic. When the stretched elastomeric is released, it contracts. The bonded non-elastic web material is forced to contract with the elastomeric causing the unbonded web to bunch together.

A similar reduction in elasticity occurs when a web and elastic are adhesively laminated. For example, diapers use an elastic laminated between two other web materials, which greatly reduces the elastic capability of the underlying elastic. Various means have been used to recapture this elasticity including ring rolling the web prior to laminating, or, ultrasonically cutting the elastic. However, the recovery of the lost elasticity has remained relatively small. Ring rolling can also result in other undesirable manifestations including cuts in the laminated web structure, partial damage to the elastic, and degradation of the appearance of the laminate finish.

There is a need for a method for regaining the elasticity of an elastic and web laminate. Improvements in the physical properties for materials such as breathable films are also needed. An ultrasonic device that allows continuous ultrasonic treatment of a workpiece without the use of rotary ultrasonic equipment may also be desirable in certain applications.

SUMMARY OF THE INVENTION

The present invention addresses the deficiencies of the prior art by providing a method and apparatus to achieve material property changes in a workpiece with ultrasonic energy. The method includes providing a horn with a first set of activation teeth having a pitch. The horn is adapted to produce ultrasonic energy with a frequency and amplitude. An anvil is provided with a second set of activation teeth having a pitch. The second set of activation teeth is disposed opposite the first set of activation teeth. The workpiece is placed between the first set of activation teeth and the second set of activation teeth. The first set of activation teeth and the second set of activation teeth mesh with each other, thereby engaging the workpiece with a depth of engagement and a clearance. The clearance combined with the depth of engagement between opposing sets of activation teeth allows the workpiece to be placed in tension between adjacent tooth tips. Ultrasonic energy is applied to the first set of activation teeth.

The ultrasonic device includes a horn with a first set of activation teeth having a pitch, height and length. The horn is adapted to produce ultrasonic energy with a frequency and amplitude. The ultrasonic device also includes an anvil with a second set of activation teeth having a pitch, height and length. The second set of activation teeth is disposed opposite and parallel to the first set of activation teeth. The two sets of activation teeth have an increasing tooth depth of engagement that progressively increases in a longitudinal direction creating a region of lesser tooth engagement and a region of greater tooth engagement.

BRIEF DESCRIPTION OF THE DRAWINGS

Embodiments with similar components may have similar reference number for clarity in the description.

DETAILED DESCRIPTION OF THE INVENTION

The invention herein is described in an illustrative manner and many modifications and variations of the invention are possible. The present invention includes a method and apparatus for changing the physical properties of a workpiece by applying ultrasonic energy. Particularly, the method and apparatus of the present invention provide a means, through the use of ultrasonic energy, for improving the elasticity of elastomeric and web bonded laminates.

Figure 2A:
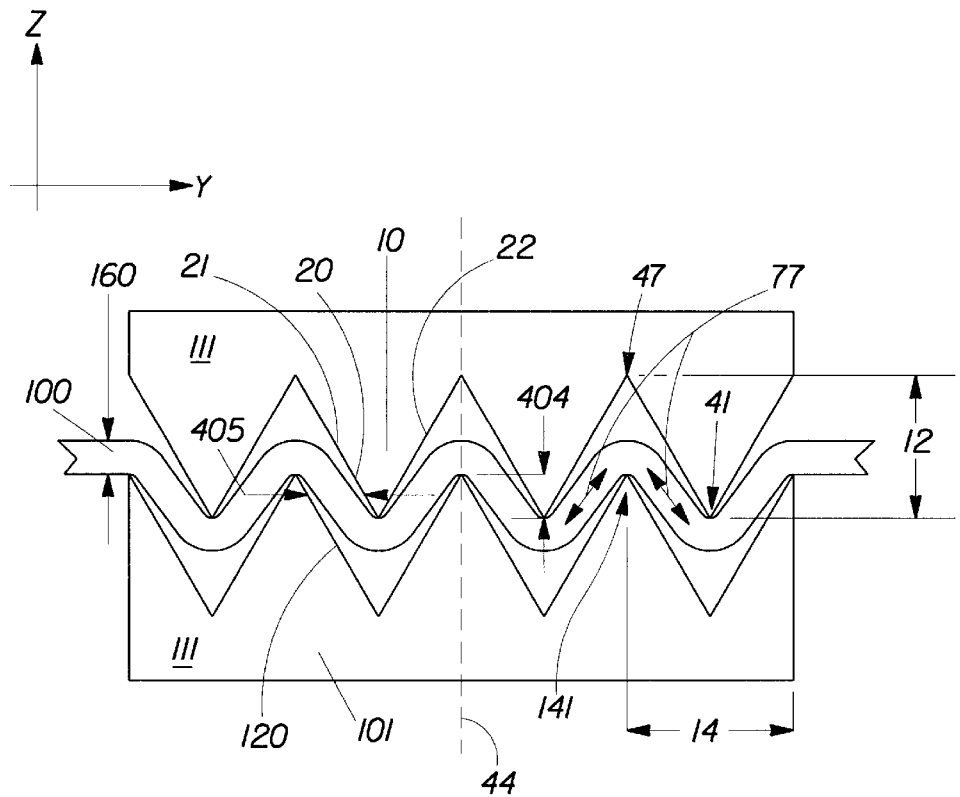
FIGS. 2a–b are cross section views of one embodiment of the ultrasonic device activation teeth.

The workpiece 100 comprises a material to be altered by the present invention. The workpiece 100 is generally in a planar configuration with a thickness 160 as shown in FIG. 2a. The workpiece may be composed of a material that is single layered, multilayered, bonded, un-bonded, woven, non-woven, knitted, non-knitted, film, laminate or a combination thereof. For example, a bonded multilayer material may include a laminate of a non-woven fibrous material and an elastomeric film. Alternatively, the workpiece may also be a fiber, collection of fibers, elastomeric film, thermoplastic, or laminate. Available workpiece materials include wool, polyester, acrylic, polytetrafluoroethylene (P.T.F.E.), nylon, Gortex™, Rayon, cotton, polymer bonded cellulose fiber, metalized film, metal foil, or a combination thereof.

Figure 1:
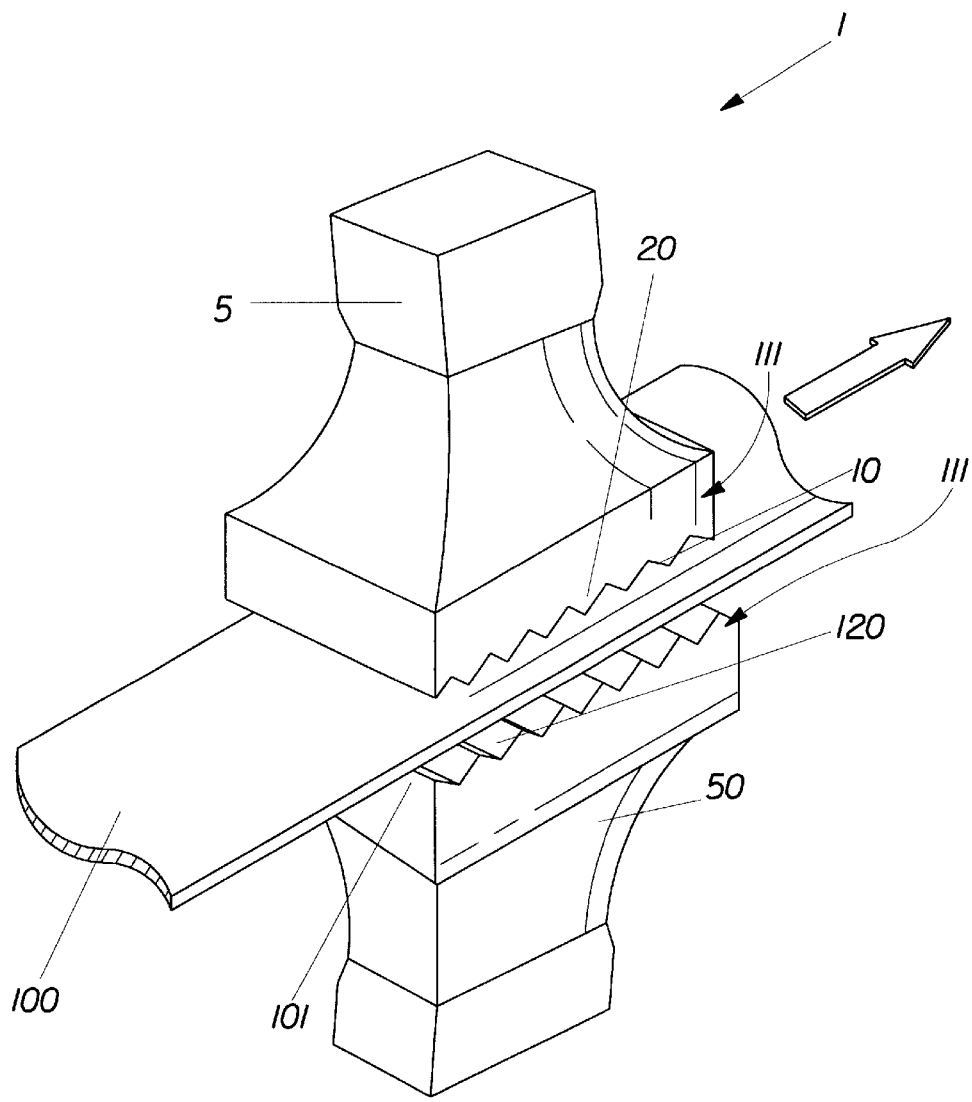
FIG. 1 is a perspective view of one embodiment of the ultrasonic device.

One apparatus for use with the present method is an ultrasonic device 1 as shown in FIG. 1. The ultrasonic device 1 has a horn 5 with a first set of activation teeth 10 and an anvil 50 with a second set of activation teeth 101. One first tooth 20 may be disposed on the first set of activation teeth 10 and another second tooth 120 may be disposed on the second set of activation teeth 101. However, as used herein any component part or description of the first set of activation teeth 10 may also apply to the second set of activation teeth 101. Generally, the horn 5 and anvil 50 are arranged so that the first set of activation teeth 10 opposes the second set of activation teeth 101 in a face-to-face arrangement as shown in FIG. 1. This forms two sets of activation teeth 111. The horn 5 is adapted to produce ultrasonic energy with a frequency and amplitude. When activated, the horn 5 provides ultrasonic energy that vibrates the first set of activation teeth 10. In this manner, the ultrasonic activation is applied to the workpiece 100. Generally, the activation teeth are protuberances extending from opposing surfaces of the horn 5 and anvil 50. The two sets of activation teeth 111 may be protuberances on opposing generally flat surfaces of the horn 5 and anvil 50 and brought together in a linear fashion, as shown in FIG. 1. Alternatively, the opposing two sets of activation teeth 111 may be brought together in a rotary fashion similar to the meshing of gear teeth on a curved anvil and/or horn surface such as a ring roll. In any case, the teeth are designed to mesh with the workpiece 100 disposed between the two sets of activation teeth 111.

The first set of activation teeth 10 and the second set of activation teeth 101 may engage the workpiece 100 that lies between them in tension 77 as shown in FIG. 2a. Tension 77 is desirable because it allows for a higher level of ultrasonic energy application without cutting or welding the workpiece 100 than is otherwise possible in a compressive loading configuration. In order to place the workpiece 100 in tension 77, a depth of engagement 404 and a clearance 405 is achieved between the opposing two sets of activation teeth 111. Workpiece tension 77 is a load between the first tooth tip 41 of one set of activation teeth and an adjacent second tooth tip 141 of another set of activation teeth, e.g. the first set of activation teeth 10 and the second set of activation teeth 101. The workpiece 100 is gripped between the two sets of teeth and put in tension 77 as the depth of engagement 404 increases. The workpiece tensile 77 loading may extend across the first tooth tip 41 and second tooth tip 141.

Figure 2B:
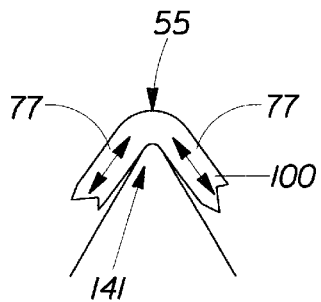

The two sets of activation teeth 111 do not meet tooth tip 41 to tooth tip 141 with the workpiece 100 between them. Tip to tip contact, or in some applications a tip to flat plate contact, causes a primarily compressive load on the workpiece and is more appropriately used for ultrasonic cutting or welding. Tip to tip contact with the workpiece disposed between the tips, or other compressive contact, results in workpiece compression rather than tension 77. FIG. 2b shows that the present invention limits the compression loading to an asymmetrical compression load 55 on the workpiece 100 across the tooth tip 141 as the workpiece 100 is pulled down in tension 77. There is no corresponding compressive load from a tooth tip 41 or plate on the side of the workpiece opposite tooth tip 141.

FIG. 2a is a close-up of the interaction between the first set of activation teeth 10, the workpiece 100, and the second set of activation teeth 101. The clearance 405 between the first set of activation teeth 10 and the second set of activation teeth 101 is shown in FIG. 2a. Clearance 405 refers to the shortest distance between a tooth 20 of the first set of activation teeth 10 and a second tooth 120 of the second set of activation teeth 101 at a given depth of engagement 404. The depth of engagement 404 is the distance a tooth 20 in the first set of activation teeth 10 will overlap an adjacent tooth 120 in the second set of activation teeth 101 when the two teeth are meshed together at a given time during the activation process. The clearance 405 may change as the two sets of activation teeth 111 come together to a desired depth of engagement 404.

The horn 5 may include a transducer that produces mechanical vibrations at ultrasonic frequency and is attached through a booster apparatus to cause ultrasonic movement or activation of the horn 5 and first set of activation teeth 10. The ultrasonic energy may be applied selectively at specific locations on the workpiece 100 or it may be applied uniformly throughout the workpiece 100 depending on the physical property changes desired in the workpiece 100.

Figure 3A:
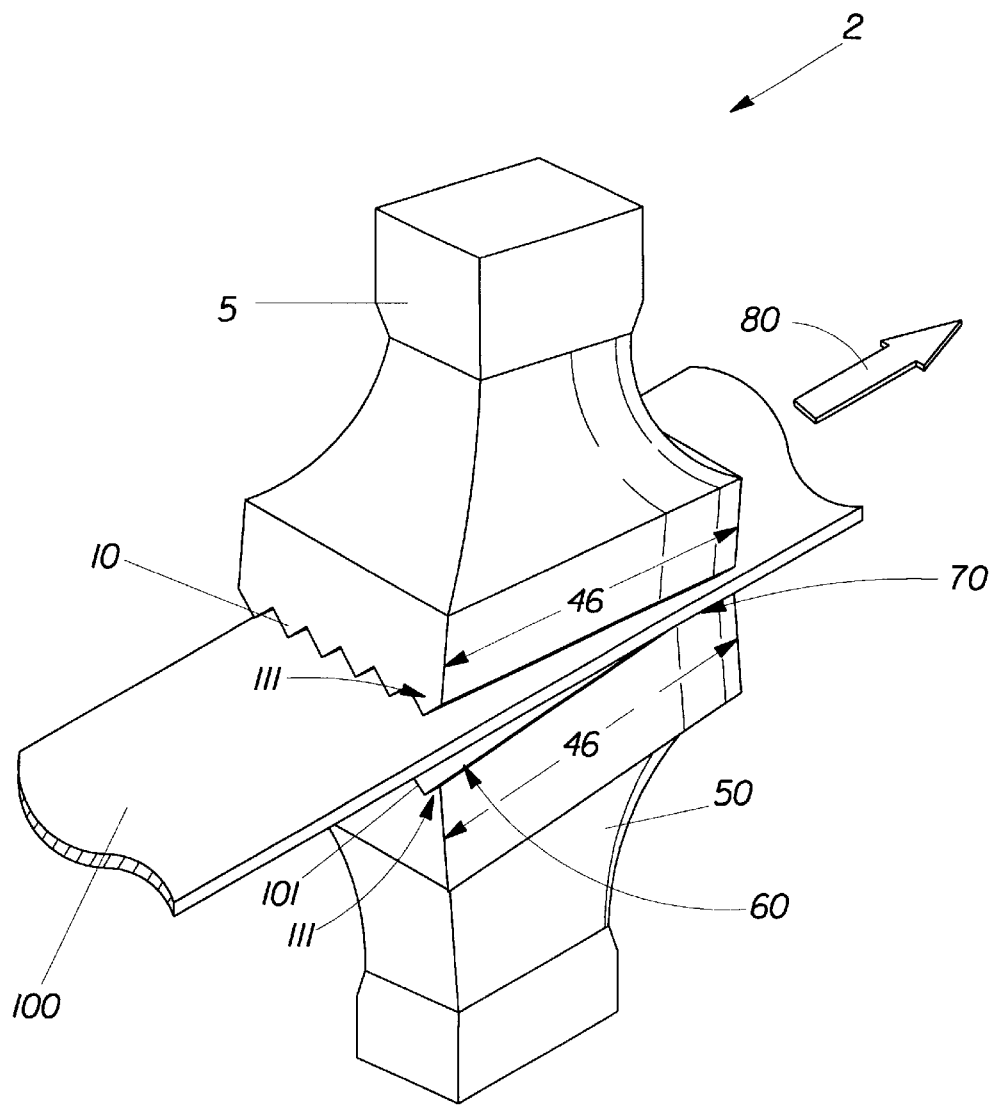
FIGS. 3a–b are perspective views of one embodiment of the ultrasonic device.
Figure 3B:
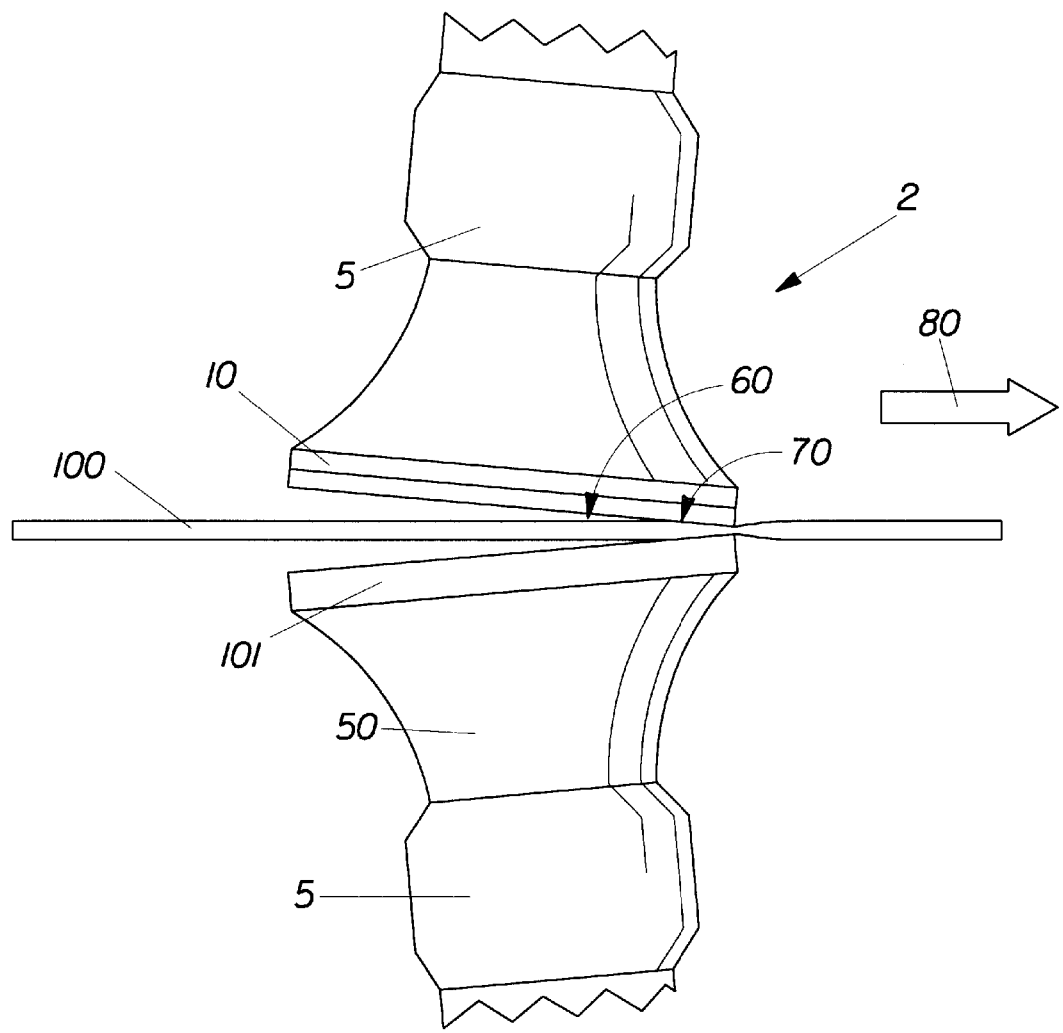

The ultrasonic device 2 depicted in FIGS. 3a–b may provide a continuous ultrasonic treatment to the workpiece 100. The ultrasonic device 2 includes a horn 5 with a first set of activation teeth 10 and an anvil 50 with a second set of activation teeth 101. The teeth in both sets of activation teeth 111 are disposed in an opposing or face-to-face relationship with the clearance 405 there between as shown in FIG. 2a. The two sets of activation teeth 111 have a depth of engagement 404 that progressively increases in a longitudinal direction 80 between opposing teeth. The longitudinal direction 80 is the direction the workpiece 100 travels. The increasing depth of engagement 404 may be created by placing one or both sets of activation teeth 111 at an inclined angle in the longitudinal direction 80 as shown in FIG. 3a. In the ultrasonic device 2, the longitudinal direction 80 is from a region of lesser tooth depth of engagement 60 to a region of greater tooth depth of engagement 70. In the ultrasonic device 2 embodiment shown in FIGS. 3a and 3b, the workpiece 100 may travel in the longitudinal direction 80 at a relatively constant speed without pausing for the application of ultrasonic energy. As the workpiece 100 travels from the region of lesser tooth depth of engagement 60 to the region of greater tooth depth of engagement 70, the workpiece 100 receives an incremental increase in activation as the depth of engagement 404 increases. The incremental increase in depth of engagement 404 in it longitudinal direction 80 allows the workpiece 100 to travel between the two sets of activation teeth without pausing for activation.

The progression of the workpiece 100 through the two sets of activation teeth 111 may be assisted by the ultrasonic energy. The ultrasonic energy frequency and amplitude assist in reducing the coefficient of friction between the workpiece 100 and the two sets of activation teeth 111 as the workpiece 100 travels between the sets of activation teeth. Generally, the first set of activation teeth 10 and the second set of activation teeth 101 are in parallel rows. The two sets of activation teeth 111 run parallel to each other and parallel to the direction of travel of the workpiece 100 (longitudinal direction 80). The first and second sets of activation teeth both have a pitch 14, which is shown in FIG. 2a on the second set of activation teeth 101. The pitch 14 represents the normal (perpendicular) distance from the vertical centerline of one tooth to the vertical centerline of an adjacent tooth in the same set of activation teeth. A smaller pitch 14, which places the teeth closer together, will generally transmit more energy throughout the workpiece 100. A larger pitch 14, which places the teeth further apart, will generally transmit less energy throughout the workpiece 100 and may reduce the impact of the ultrasonic energy on the workpiece 100.

The pitch 14 of the first set of activation teeth 10 and/or the second set of activation teeth 101 may be any suitable pitch. However, placing the activation teeth too close together may reduce the depth of engagement 404 and the amount of workpiece 100 that is placed in tension 77. Pitch 14 has generally been found to be suitable in the range of between about 0.002 inches and about 2 inches, or more preferably between about 0.08 inches and about 1 inch. Generally, as shown in FIG. 3a, the pitch 14 for ultrasonic device 2 is perpendicular to the longitudinal direction.

Figure 4A:
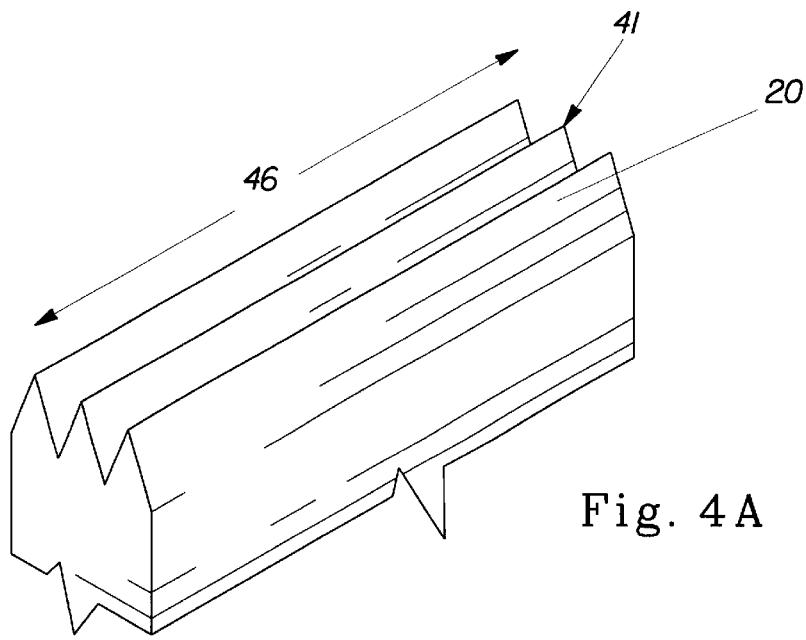
FIGS. 4a–d are perspective views of an alternate embodiment of the activation teeth.
Figure 4B:
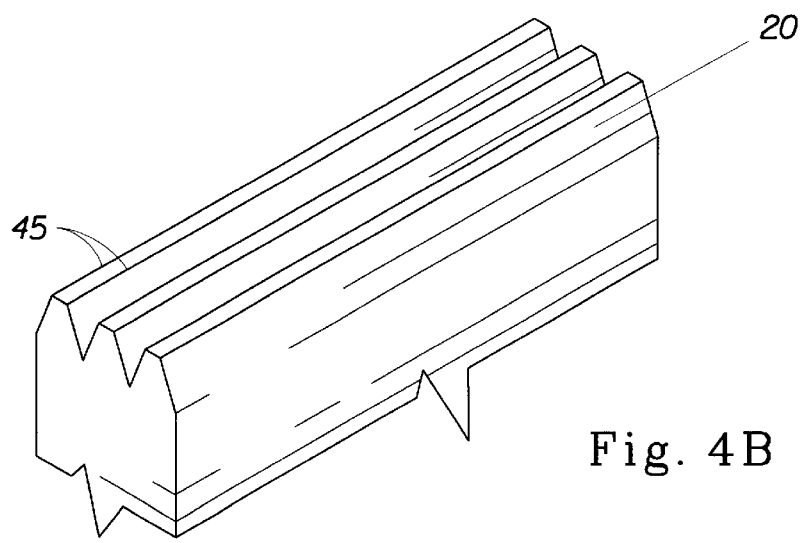
Figure 4C:
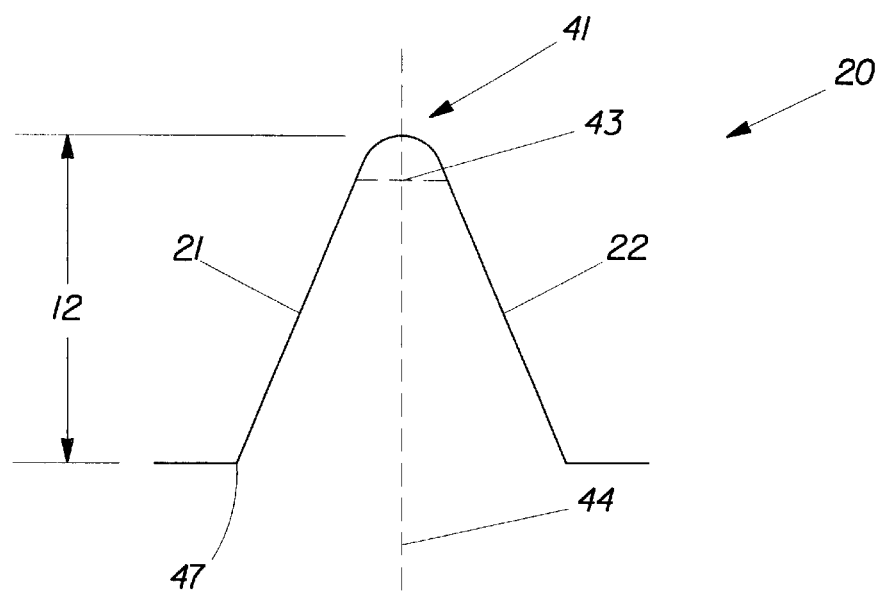
Figure 4D:
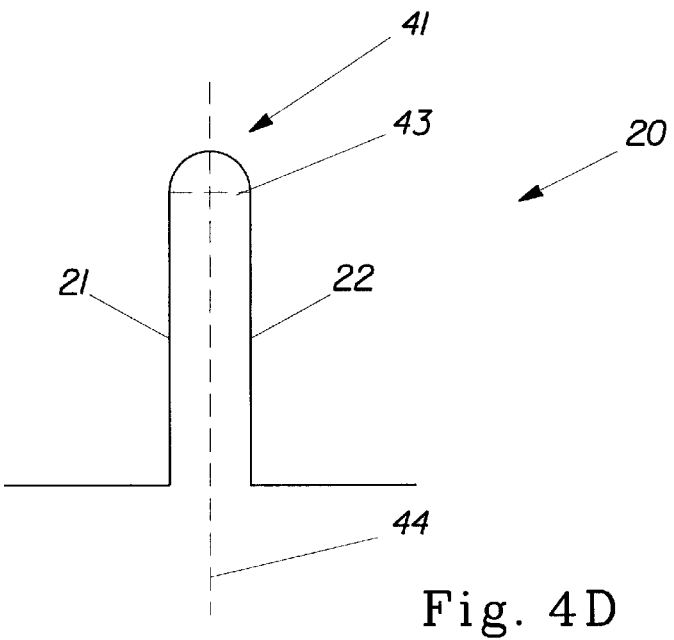

Typically, the activation teeth are machined into the horn 5 or anvil 50. However, the activation teeth may be separate elements joined to the horn 5 or anvil 50. The teeth may extend for any suitable tooth length 46 on the two sets of activation teeth 111 as shown in FIGS. 3a and 4a. Each tooth 20 has a first side 21, a second side 22, and a tooth tip 41 as shown in FIGS. 2a, 4c and 4d. The teeth may have any appropriate first side 21 or second side 22 structure. Some possible side structures are shown in FIGS. 2, 4a–d, 5, and 6. Preferably, the tooth tip 41 will have a tooth tip radius 43 that provides a rounded configuration as shown in FIGS. 4c and 4d. The tooth tip radius 43 defines the rounding of the tooth tip 41 on a radius from a point along a centerline 44 of the tooth 20. A true radius of a circle is preferred for the tooth tip radius 43 over an oval to maintain a constant friction grip on the material across the tooth tip. The tooth tip may be any suitable radius. However, a tooth tip radius 43 of at least about 0.005 inches is preferred in order to avoid cutting the workpiece during activation. Alternatively, the tooth tip 41 may be flat with radiused corners 45 as shown in FIG. 4b.

The teeth from the first set of activation teeth 10 and the second set of activation teeth 101 as shown in FIGS. 2a and 4c, each have a corresponding tooth height(s) 12. The tooth height 12 (or tooth depth) is the vertical perpendicular distance from a tooth bottom 47 (the root radius) to the top of the tooth tip 41 at a given point. The tooth height 12 may be any suitable height. For example the tooth height 12 may be from about 0.005 inches to about 5 inches, about 0.005 inches to about 2 inches, about 0.05 inches to about 0.5 inches, or about 0.05 inches to about 3 inches.

Figure 5:
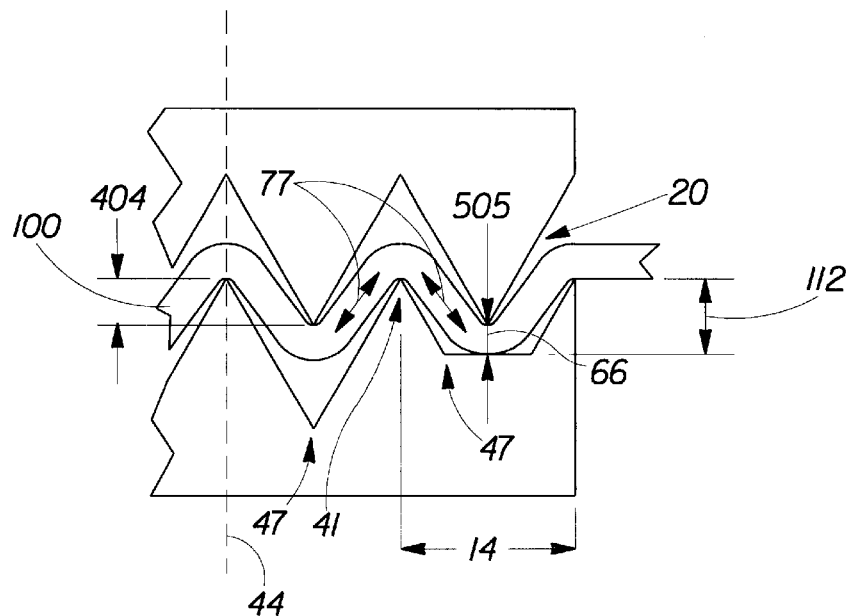
FIG. 5 is a cross section view of one embodiment of the ultrasonic device activation teeth.

Generally, the tooth dimensions may be selected independently such that they bare no relationship to one another. Alternatively, the tooth dimensions may have some preferred relationships. For instance, it may be preferred in some embodiments that the tooth tip radius 43 not exceed ¼ of the tooth height 12 to avoid excessive workpiece contact with the tooth tip 41. Excessive contact may cause gripping and reduce the tension 77 in the workpiece 100. In addition, the tooth may have two different tooth heights 12 measured from either side of the tooth 20. The distance from the tooth bottom 47 to the tooth tip 41 measured from a tooth first side 21 may be different than what is measured from a tooth second side 22. One embodiment with varying tooth height 112 is shown in FIG. 5, discussed below. Varying tooth height(s) 12 may be used to create the region of lesser tooth depth of engagement 60 and the region of greater tooth depth of engagement 70 as previously described. For instance, the depth of engagement 404 between the two sets of activation teeth 111 may be progressively increased by increasing the tooth height 12 along the tooth length 46 in the longitudinal direction 80. Generally, for ultrasonic device 2, it is preferred that the tooth length 46 be parallel to the longitudinal direction 80.

Each set of activation teeth may have a same tooth pattern wherein each tooth has the same height 12, pitch 14 and design as the other teeth in the set of activation teeth. Alternatively, each set of activation teeth may have a different tooth pattern wherein some or all the teeth may have a different height 12, pitch 14 and design. For instance, the teeth disposed on opposite sets of activation teeth may not be in the same location relative to one another. In one embodiment, the first set of activation teeth 10 and the second set of activation teeth 101 may be machined to varying tooth heights 12 in order to provide selective ultrasonic energy applications to the workpiece 100. Regions of lesser tooth depth of engagement 404 due to shorter tooth height 12 generally provide less ultrasonic activation of the workpiece than a region with greater tooth depth of engagement 404 due to longer tooth height 12.

The depth of engagement 404 in FIG. 2a may vary during workpiece activation as the first set of activation teeth 10 oscillate with a frequency and amplitude. The ratio of depth of engagement 404 to pitch 14 refers to the depth of the tooth engagement of a tooth 20 at a particular point divided by the tooth pitch 14 at that point. For example, a depth of engagement 404 to pitch 14 ratio of 1:6 could result from a tooth depth of engagement 404 of 0.01 inches and pitch 14 of 0.06 inches. On the other hand, a depth of engagement 404 to pitch 14 ratio of 20:1 could result from a depth of engagement 404 of 1 inch and a pitch 14 of 0.05 inches. All or part of the depth of engagement 404 may result from the ultrasonic activation amplitude or mechanical placement of the two sets of activation teeth. While operating, the ultrasonic device 1 may have a depth of engagement 404 to pitch 14 ratio of between about 1:100 and about 20:1, about 1:100 and about 5:1, about 1:10 and about 10:1, or about 1:10 and about 20:1.

Figure 6:
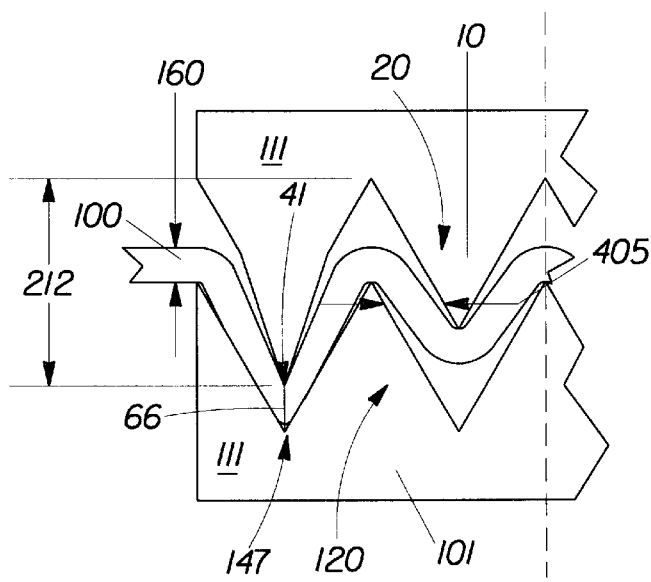
FIG. 6 is a cross section view of one embodiment of the ultrasonic device activation teeth.

Preferably, the workpiece 100 is in tension 77 during activation since compression 66 may result in unintended welding (bonding) or cutting of the workpiece 100. Compressive loading 66 may occur during activation in FIG. 2a when the clearance 405 between the first set of activation teeth 10 and the second set of activation teeth 101 is less than the workpiece thickness 160. Two embodiments with compression are shown in FIGS. 5 and 6. FIG. 5 shows compression 66 at clearance 505. FIG. 6 shows compression 66 between tooth tip 41 and tooth bottom 147. Decreasing the depth of engagement 404 to pitch 14 ratio may avoid compressive loading in the y and/or z direction of FIG. 2a. The compressive loading may also be avoided by having a depth of engagement 404 that is less than the workpiece thickness 160, or providing a clearance 405 that is greater than the workpiece thickness 160. Either a depth of engagement 404 that is less than the workpiece thickness 160, or a clearance 405 that is greater than the workpiece thickness 160 may place the workpiece in tension 77, rather than compression 66. A straight-sided tooth as shown in FIG. 4d, meshed as shown in FIG. 2a, combined with a thin workpiece 100 and a wide pitch 14 may create the capability for a larger depth of engagement 404 and therefore, a larger depth of engagement 404 to pitch 14 ratios. The selection of a particular depth of engagement 404 to pitch 14 ratio represents an area of variation for specific material applications.

The application of ultrasonic energy as described may result in a high strain rate on the workpiece 100. Where the workpiece 100 contains fibers, the high strain rate can contribute to internal fiber bond relaxation and stress relaxation which intern can affect the workpiece 100 material property changes. Examples of internal fiber bond relaxation because of a reduction in friction and other forces between fibers can be found in the book Manual of Nonwovens, by Professor Radko Krčma, on pages 38–3. This book is incorporated herein by reference.

The ultrasonic process of the present invention may cause workpiece stress relaxation. Workpiece stress relaxation includes "loosening" a workpiece comprising a fiber web by reducing the friction between web fibers after activation, straightening the web fibers at the areas of activation and/or stretching the fiber (fiber elongation) within the region of activation. Fiber elongation occurs when the distance between two points on a fiber increases as a result of the ultrasonic activation. Workpiece stress relaxation may also include the relaxation of internal fiber forces including bonds between fibers that hold the fiber in a particular orientation, as well as bonds between fibers and films. The stress relaxation may increase the flexibility of the workpiece and make it less brittle, or make it more elastic when the workpiece includes an elastomeric film. Some fiber bonds may additionally be fractured, broken, or otherwise degraded in the process. Stress relaxation may occur on the workpiece outer layer, inner layer or any other layer as desired and controlled through process manipulation. The process may also reduce fiber stress concentration points resulting from geometric discontinuities.

Internal fiber stress relaxation takes place as the two sets of activation teeth 111 rapidly and repeatedly engage the workpiece 100. The repeated tooth engagement and workpiece 100 activation may occur before the workpiece 100 has fully returned to its unengaged and unactivated orientation. This process may result in repeated tensile loading before the workpiece 100 has had time to completely respond to the release of the previous tensile load imposed by the meshing of the two sets of activation teeth 111. The rapid reengagement and activation of the workpiece 100 before it has returned to its unengaged and unactivated state may contribute to the advantageous results of the present invention described below. In addition, repeated engagement with a smaller depth of engagement 404 and smaller ultrasonic amplitude may assist in minimizing any unintended fiber or film breaking.

By modifying the apparatus or method of the present invention, the workpiece 100 may be selectively activated with ultrasonic energy to provide varying levels of elasticity, surface loft, and extensibility. In one embodiment the workpiece 100 includes an elastomeric or elastomeric and web laminate. For this embodiment, the elasticity of the workpiece 100 may be increased such that the elastic material may stretch further and retract to approximately the original length, with less material thickness. The method herein may increase the elasticity of the initial, pre-activation workpiece 100 from about 5% to about 800%, about 10% to about 400%, or 200% to about 800%.

Surface loft refers to the caliper of the workpiece thickness 160 in the z direction as shown in FIG. 2a. Surface loft may be increased by loosening or breaking material bonds, which allows the workpiece material to separate in the z direction, thus creating a thicker and/or softer material. The method herein disclosed may result in an increase in the workpiece surface loft ranging from at least about 50% to about 300%, about 200% to about 300%, or about 50% to about 200%.

Extensibility of a workpiece 100, which preferably includes an elastomeric laminate, may also be improved. Extensibility is the ability of the workpiece to stretch or extend itself under a load, although the workpiece 100 may not retract when the load is released. The method and/or apparatus herein disclosed may result in an increase in extensibility of about 60% to about 300%, about 10% to about 160%, about 15% to about 95%, or by more than about 30%.

The present invention may be used to create a breathable film from a workpiece 100 of film containing voiding aggregates. Voiding aggregates include pore inducing polymer film matrix filler particles. A breathable film allows the transfer of vapor such as water vapor and air through the film. The ultrasonic activation stretches the film around the voiding aggregate and "shakes" the voiding aggregates out with less film tearing around the aggregates than the prior art which stretches and or shakes the particles out of the film. The voids are used to create a path for vapor to escape. Tearing may create a path for liquid to also penetrate. Examples of films containing pore inducing polymer film matrix filler particles are disclosed in U.S. Pat. No. 4,705,812, Keiko et al., which is incorporated herein by reference. The pore inducing polymer film matrix filler particles may be a calcium carbonate, titanium dioxide, barium sulfate, or any pore inducing polymer film contaminate known in the art, as well as combinations thereof. In certain embodiments, e.g. breathable backsheets for absorbent articles, the pore inducing polymer film matrix filler particles may have an average diameter of between about 0.1 microns and about 10 microns.

The workpiece thickness 160, coefficient of friction, and material type may have an effect on how the workpiece 100 reacts to the ultrasonic activation as well as the ease with which the process may be used. Generally, a thinner workpiece 100 consisting of materials with lower coefficients of friction allow a deeper depth of engagement 404 for a given tooth pitch 14. The deeper depth of engagement 404 may be possible in part because the "gripping" effect at the points of contact between the workpiece 100 and the two sets of activation teeth 111 is lowered with lower coefficients of friction.

Numerous modifications of the ultrasonic device and method herein described are envisioned. For example, the two sets of activation teeth 111 may mesh opposite one another in a flat or horizontal relationship as shown in FIG. 1, they may mesh at an angle opposite one another as shown in FIG. 3a and 3b, or mesh as a rotary device such as mating ring rolls. In addition, the ultrasonic device may comprise multiple horns 5 and/or anvils 50 in any combination or configuration known in the art. Multiple horn 5 and/or anvil embodiments can have multiple sets of activation teeth 111 configured to oppose each other with the workpiece 100 between them.

Alternatively, the anvil 50 may be replaced by a second horn that also supplies ultrasonic activation to the workpiece 100. A second horn may be preferred for some embodiments, such as the one shown in FIG. 3, to decrease the coefficient of friction between the sets of activation teeth 111 and the workpiece 100. When two horns are used, each horn will generally produce ultrasonic energy with at least one different frequency, amplitude, time of application, or direction of application with respect to a fixed point. The frequencies of the two horns may also be out of phase. The frequency of the ultrasonic energy produced by the first horn, second horn, or any horn used herein may be at least about 16 kHz to about 1 GHz, or about 16 kHz to about 10 MHz, or about 18 kHz to about 9 MHz, or about 60 kHz to about 6 MHz. Amplitude is defined as the highest point of periodic movement of the activation teeth. The amplitude range of the ultrasonic energy produced by the first horn, second horn, or any horn used herein may be about 0.0002 inches to about 0.1 inches, about 0.0002 inches to about 0.05 inches, or about 0.02 inches to about 0.1 inches.

The ultrasonic energy may be applied at any time during the process. For example, the workpiece 100 may be engaged between the two sets of activation teeth 111 at a desired depth of engagement 404 and the ultrasonic energy subsequently applied. Alternatively, the ultrasonic energy may be continuously applied as the workpiece 100 moves between the two sets of activation teeth 111. The choice of activation time depends in part upon the material of the workpiece 100 and the characteristics of the change desired. The ultrasonic energy may be applied over any suitable period of time. For typical film, woven and non-woven workpieces it has been found that a period from about 0.00001 of a second to about 5 seconds, or preferably from about 0.00001 to about 1 second is suitable.

The following is a non-limiting example of a method for improving an elastomeric laminate's elasticity. (See FIGS. 1, 2, and 4c). A horn 5 with a first set of activation teeth 10 having a pitch 14 of about 0.06 inches and a tooth tip radius 43 of between about 0.0056 inches and about 0.0059 inches, is disposed opposite an anvil 50. The anvil 50 has a second set of activation teeth having a pitch 14 of about 0.06 inches and a tip radius 43 of about 0.0058 inches. The first set of activation teeth 10 and the second set of activation teeth are disposed in a facing relationship such that they mesh with one another. The workpiece 100, an adhesively bonded vacuum formed elastomeric (VFE) trilaminate, is placed between the first set of activation teeth 10 and the second set of activation teeth 101. The workpiece 100 is engaged in tension between the two sets of activation teeth 111 with a depth of engagement 404 of about 0.098, an amplitude of about 0.0012 inches and a frequency of about 20 kHz. A workpiece 100 that is activated may have a doubling in stretch capability with less than about 400 grams per 25 mm width of load. It may take over about 800 grams per 25 mm of width loading to double the stretch of a workpiece 100 when the material is subject to mechanical activation alone.

The following is a non-limiting example of a method for creating a breathable film. A horn 5 with a first set of activation teeth 10 having a pitch 14 of about 0.06 inches and a tooth tip radius 43 of between about 0.0056 inches and about 0.0059 inches, is combined with an anvil 50 with a second set of activation teeth 101 having a pitch 14 of about 0.06 inches and a tip radius 43 of between about 0.0056 inches and about 0.0059 inches. Both sets of teeth are in a ridged configuration as shown in FIG. 1 with parallel sets of activation teeth 111 in a linear, perpendicular relationship. The first set of activation teeth 10 and the second set of activation teeth 101 are placed in a facing relationship such that they mesh with one another. The workpiece 100, a Clopay precursor film EXP-5092, is placed between the first set of activation teeth 10 and the second set of activation teeth 101. The workpiece 100 is engaged in tension 77 between the two sets of activation teeth 111 with a depth of engagement 404 of about 0.02 inches, an amplitude of about 0.0012 inches and a frequency of about 20 kHz. The resulting workpiece 100 material, with ultrasonic activation, may have a moisture vapor transmission rate of over about 1500 grams per square meter in 24 hours. In contrast, a workpiece 100 material with only mechanical activation to a depth of engagement 404 of 0.02 inches may have a moisture vapor transmission of about 500 grams per square meter in 24 hours. As the depth of engagement 404 increases, the difference in vapor transmission decreases. However, the increasing depth of engagement 404 also increases workpiece 100 material perforations, which may allow the transmission of both liquid and vapor moisture. Liquid transmission may be undesirable in many applications such as the backsheet of a diaper and rain gear.

The following is another non-limiting example of an ultrasonic device 2 for creating a breathable film as shown in FIGS. 3a and 3b. A horn 5 with a first set of activation teeth 10 having a pitch 14 of about 0.06 inches and a tooth tip radius 43 of between about 0.0056 inches and about 0.0059 inches, is combined with an anvil 50 with a second set of activation teeth 101 having a pitch 14 of 0.06 inches and a tip radius 43 of about 0.0058 inches. The first set of activation teeth 10 and the second set of activation teeth 101 are placed in a facing relationship such that they mesh with one another as shown in FIGS. 3a–b. The two sets of activation teeth 111 are in a vertical angled relationship in the z direction as shown in FIG. 3b. Note that the angles are exaggerated to facilitate illustrative purpose of FIG. 3b. The horn 5 is horizontal and the anvil 50 is raised at one end about 0.05 inches or at an angle of about 0.57 degrees incline toward the first set of activation teeth 10. The workpiece 100, a Clopay precursor film EXP-5092, is placed between the first set of activation teeth 10 and the second set of activation teeth 101. The workpiece 100 is pulled in the longitudinal direction 80 through the two sets of activation teeth 111 from the region of lesser depth of engagement 60 through the region of greater depth of engagement 70 while the horn 5 produces an ultrasonic energy at an amplitude of about 0.0012 inches and a frequency of about 20 kHz. The workpiece 100 is engaged between the first set of activation teeth 10 and the second set of activation teeth 101. The workpiece 100 is in tension 77 between the tooth tips while passing from the region of lesser depth of engagement 60 to the region of greater depth of engagement 60. The resulting workpiece 100, after ultrasonic activation at a depth of engagement 404 of about 0.035 inches may have a moisture vapor transmission rate of over about 3700 grams per square meter in 24 hours.

In another embodiment, activating portions of the workpiece 100 may be combined with compressing portions of the workpiece 100. Compression 66 may be used to cut, bond, and/or hold portions of the workpiece 100 at the point of compression 66. Compression 66 in combination with activation can be performed by placing a first part of the workpiece 100 in tension 77 simultaneous with placing a second part of the workpiece in compression 66 and applying ultrasonic energy. For this embodiment, one or more teeth in opposing two sets of activation teeth 111 may be made to cause tension in a first part of the workpiece 100 when meshed with a depth of engagement 404 and a clearance 405 that is greater than the workpiece thickness 160 while at the same time, one or more teeth in the same two sets of activation teeth 111 may be made to cause compression 66 in a second part of the workpiece when meshed with a depth of engagement 404 and a clearance 405 that is less than the workpiece thickness 160. Compression 66 combined with ultrasonic energy may cause bonding or cutting of certain parts of the workpiece 100, while other parts of the workpiece 100 are activated in tension 77 to achieve other physical property modifications.

An example of this embodiment is illustrated in FIG. 5. For this embodiment, either the first set of activation teeth 10 or the second set of activation teeth 101 includes one or more teeth having a shorter tooth height 112 than the remaining teeth. The reduction in tooth height 112 reduces the clearance 505 between the two sets of activation teeth 111 and causes the workpiece 100 to be in compression 66 at that location when the teeth are meshed with a depth of engagement 404. Generally, to create compression 66 the clearance 505 is less than the workpiece thickness 160. Under compression 66, the workpiece 100 may be bonded to another layer of the workpiece 100 or cut depending upon the tooth geometry and amount of ultrasonic energy applied.

Increasing a tooth height 212 as shown in FIG. 6 may also create localized compression 66. During meshing the tooth tip 41 compresses the workpiece 100 with the tooth bottom 147 (also called the tooth root radius). As with the previous embodiment, this tighter clearance can be made less than the workpiece thickness 160 in order to engage the workpiece 100 in compression 66 while the remaining teeth engage the workpiece in tension 77.

In still another embodiment, the workpiece 100 may be made thicker in the areas where cutting or bonding is desired and thinner in other areas for activation.

While particular embodiments and/or features of the present invention have been illustrated and described, it would be clear to those skilled in the art that various other changes and modifications can be made without departing from the spirit and scope of the invention. Further, it should be apparent that all combinations of such embodiments and features are possible and can result in preferred executions of the invention. Therefore, the claims herein are intended to cover all such changes and modifications that are within the scope of this invention.

What is claimed is:

1. A method of achieving a material property change in a workpiece comprising the steps of:
   providing a horn with a first set of activation teeth, the horn being adapted to produce ultrasonic energy with a frequency and amplitude;
   providing an anvil with a second set of activation teeth, the second set of activation teeth disposed opposite the first set of activation teeth;
   placing the workpiece between the first set of activation teeth and the second set of activation teeth;
   meshing the first set of activation teeth and the second set of activation teeth, thereby engaging the workpiece with a depth of engagement and a clearance in order to place the workpiece in tension; and
   applying ultrasonic energy to the first set of activation teeth.

2. The method of claim 1 wherein the workpiece has a thickness and wherein the clearance is greater than the thickness.

3. The method of claim 1 wherein the frequency is between about 16 KHz and about 1 GHz.

4. The method of claim 1 wherein the amplitude is between about 0.0002 inches and about 0.1 inches.

5. The method of claim 1 wherein the workpiece material property change includes stress relaxation.

6. The method of claim 1 wherein the workpiece includes a film, woven, non-woven, knit, laminate, or a combination thereof.

7. The method of claim 1 wherein the workpiece includes thermoplastic or elastomeric film.

8. The method of claim 1 wherein the workpiece includes wool, polyester, acrylic, polytetrafluoroethylene, nylon, rayon, cotton, polymer bonded cellulose fiber, metalized film or metal foil.

9. The method of claim 1 wherein the workpiece includes a fiber, collection of fibers, elastomeric film, thermoplastic, or laminate.

10. The method of claim 1 wherein the first set of activation teeth and the second set of activation teeth mesh as mating ring rolls.

11. The method of claim 1 wherein the frequency is between about 16 KHz and about 10 MHz.

12. The method of claim 11 wherein the first set of activation teeth have a pitch and wherein the ratio of the depth of engagement to the pitch is between about 1:100 and about 20:1.

13. The method of claim 11 wherein the workpiece material property change is an increase in extensibility of between about 60% and about 300%.

14. The method of claim 11 wherein the workpiece material property change is an increase in the workpiece surface loft of between about 50% and about 300%.

15. The method of claim 11 wherein the workpiece is an elastomeric laminate.

16. The method of claim 15 wherein the workpiece material property change is an elasticity increase of about 5% to about 800%.

17. The method of claim 1 wherein the workpiece includes a film containing pore inducing polymer film matrix filler particles and the workpiece material property change is a breathable film.

18. The method of claim 17 wherein the pore inducing polymer film matrix filler particles include calcium carbonate, titanium dioxide, or barium sulfate.

19. The method of claim 17 wherein the pore inducing polymer film matrix filler particles have an average diameter of between about 0.1 microns and about 10 microns.

20. A method of achieving at least one material property change in a workpiece comprising the steps of:
   providing at least one first horn with a first set of activation teeth, the at least one first horn being adapted to produce ultrasonic energy with a frequency and amplitude;
   providing at least one second horn with a second set of activation teeth, the at least one second horn being adapted to produce ultrasonic energy with a frequency and amplitude;
   placing the workpiece between the first set of activation teeth and the second set of activation teeth;
   meshing the first set of activation teeth and the second set of activation teeth, thereby engaging the workpiece with a depth of engagement and a clearance in order to place the workpiece in tension; and
   applying ultrasonic energy from the first horn to the first set of activation teeth and from the second horn to the second set of activation teeth.

21. The method of claim 20 wherein the amplitude of the ultrasonic energy from the first horn and the amplitude of the ultrasonic energy from the second horn are different.

22. The method of claim 20 wherein the frequency of the ultrasonic energy from the first horn and the frequency of the ultrasonic energy from the second horn are different or out of phase.

23. The method in claim 20 wherein the first set of activation teeth has a different tooth pattern than the second set of activation teeth.

24. The method in claim 20 wherein the first set of activation teeth has a same tooth pattern as the second set of activation teeth.

25. An ultrasonic device generating ultrasonic energy to change the material properties of a workpiece, the ultrasonic device comprising:
   a horn with a first set of activation teeth, the horn being adapted to produce ultrasonic energy with a frequency and amplitude; and
   an anvil with a second set of activation teeth,
      the second set of activation teeth disposed opposite and parallel to the first set of activation teeth, the first set of activation teeth mesh with the second set of activation teeth at a tooth depth of engagement that progressively increases in a longitudinal direction, creating a region of lesser tooth engagement and a region of greater tooth engagement.

26. An ultrasonic device generating ultrasonic energy to change the material properties of a workpiece, the ultrasonic device comprising:

a first horn with a first set of activation teeth, the first horn being adapted to produce ultrasonic energy with a first frequency and first amplitude; and a second horn with a second set of activation teeth, the second horn being adapted to produce ultrasonic energy with a second frequency and second amplitude;

wherein the second set of activation teeth disposed opposite and parallel to the first set of activation teeth, the first set of activation teeth mesh with the second set of activation teeth at a tooth depth of engagement that progressively increases in a longitudinal direction, creating a region of lesser tooth engagement and a region of greater tooth engagement.

27. A method of achieving more than one material property change in a workpiece comprising the steps of:

providing a horn with a first set of activation teeth, the horn being adapted to produce ultrasonic energy with a frequency and amplitude;

providing an anvil with a second set of activation teeth, the second set of activation teeth disposed opposite the first set of activation teeth;

placing the workpiece between the first set of activation teeth and the second set of activation teeth;

meshing the first set of activation teeth and the second set of activation teeth, wherein the first set of activation teeth and the second set of activation teeth engage a first part of the workpiece with a depth of engagement and a clearance which is greater than the thickness of the workpiece in order to place the first part of the workpiece in tension; and wherein the first set of activation teeth and the second set of activation teeth engage a second part of the workpiece with a depth of engagement and a clearance which is less than the thickness of the workpiece in order to place the second part of the workpiece in compression; and applying ultrasonic energy to the first set of activation teeth.

* * * * *

UNITED STATES PATENT AND TRADEMARK OFFICE
CERTIFICATE OF CORRECTION

PATENT NO. : 6,562,166 B2 Page 1 of 1
DATED : May 13, 2003
INVENTOR(S) : Molander et al.

It is certified that error appears in the above-identified patent and that said Letters Patent is hereby corrected as shown below:

Column 6,
Line 66, delete "3" and insert -- 43 --.

Signed and Sealed this

Twenty-seventh Day of April, 2004

JON W. DUDAS
*Acting Director of the United States Patent and Trademark Office*